United States Patent [19]

Durden, III

[11] 3,974,833
[45] Aug. 17, 1976

[54] DISPOSABLE ELECTROSURGICAL CAUTERY HAVING OPTIONAL SUCTION CONTROL FEATURE

[76] Inventor: John G. Durden, III, Auburn, Ga.

[22] Filed: July 22, 1974

[21] Appl. No.: 490,243

Related U.S. Application Data

[63] Continuation-in-part of Ser. No. 342,382, March 19, 1973, Pat. No. 3,825,004.

[52] U.S. Cl. .......................... 128/275.1; 128/303.17; 137/68 R
[51] Int. Cl.² .................... A61B 17/36; A61N 3/04; A61M 1/00
[58] Field of Search ................... 128/275.1, 303.17; 220/231; 137/68 R

[56] References Cited
UNITED STATES PATENTS

| | | | |
|---|---|---|---|
| 1,919,543 | 7/1933 | Doane | 128/303.17 X |
| 2,808,833 | 10/1957 | August | 128/303.17 |
| 2,888,928 | 6/1959 | Seiger | 128/303.17 |
| 3,494,363 | 2/1970 | Jackson | 128/303.17 X |
| 3,720,348 | 3/1973 | Jakobsen | 220/231 X |
| 3,825,004 | 7/1974 | Durden | 128/303.17 X |
| 3,828,780 | 8/1974 | Morrison, Jr. | 128/303.17 X |

Primary Examiner—Channing L. Pace
Attorney, Agent, or Firm—Eric P. Schellin; John E. Becker

[57] ABSTRACT

A disposable electrosurgical cautery which functions in a dual capacity as a hollow sucker tube as well as a cauterizer, and is intended to be prepackaged in sterilized preferably envelope-type containers, to be used once and disposed of. The cautery consists of an elongated hollow metal electrode and suction tube having an electrical conductor wire permanently connected to the proximal portion, and together are encased in a plastic housing which serves as an insulating handle. The handle is of special anatomically contoured configuration to provide for deft and positive use of the distal or forwardly projecting probe or point of the cautery without chance of short circuits or burns through inadequate wire connections or poor insulation. One of the more preferred embodiments forming a particular basis of this continuation-in-part application provides for a selective operative use of a suction control hole provided strategically in a forward or distal part of the handle and in a corresponding part of the electrode/suction tube, collectively. A preformed control hole in the handle is covered by a weakened integral membrane capable of being readily punched out by surgeons who prefer cauteries with this feature giving them control over the vacuum or suction in a suction-integrated electrosurgical cautery. In operation, blood from a surgical incision or other wound is drawn by vacuum through the barrel of the electrode tube, clear of the severed vessels, and a high frequency current is passed through the electrode to cauterize and prevent further bleeding of the vessels. When the control hole is desired, the weakened membrane usually is initially punched out, and which hole can be covered selectively by the finger of thumb to obtain full or partial suction at the tip of the suction tube.

38 Claims, 24 Drawing Figures

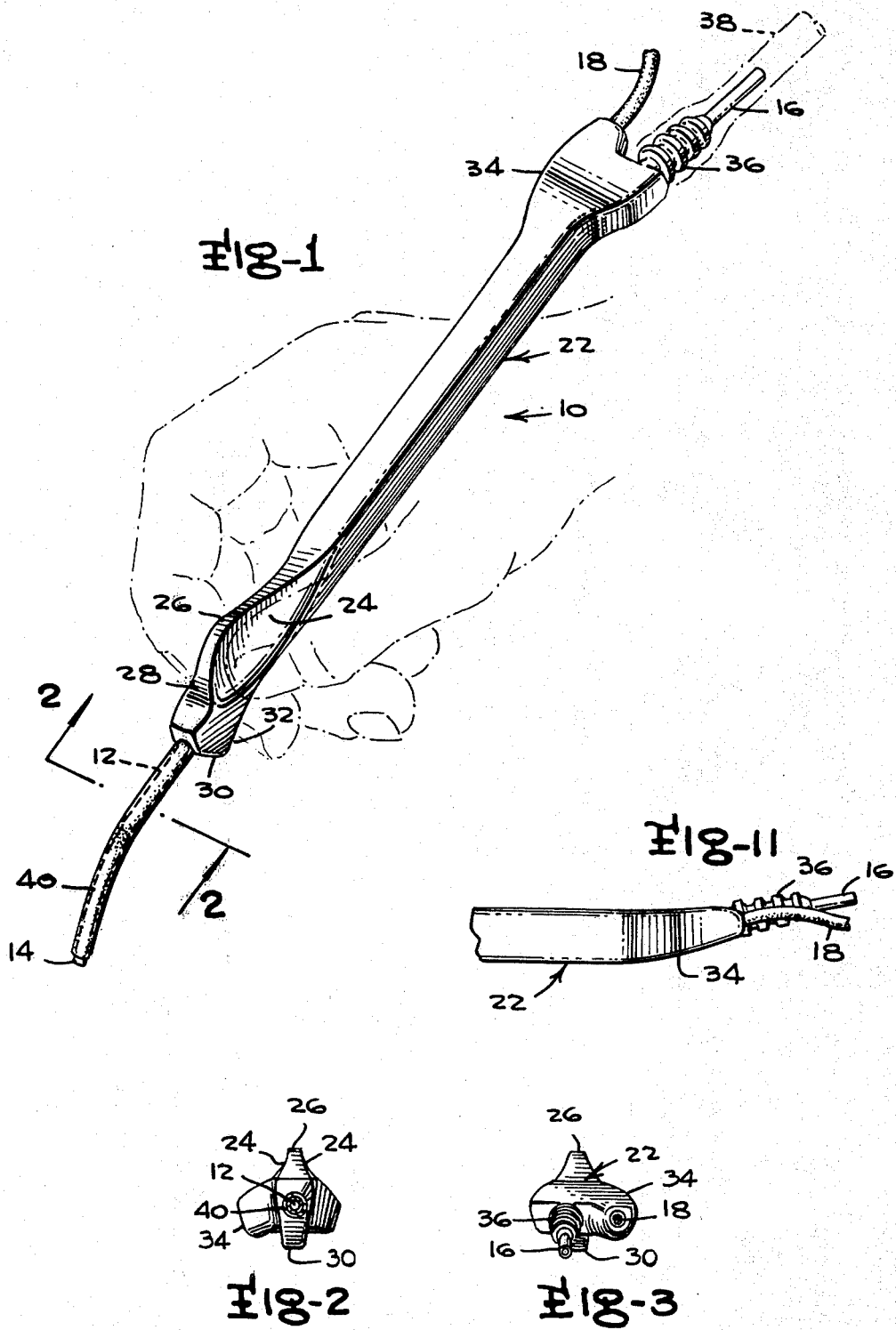

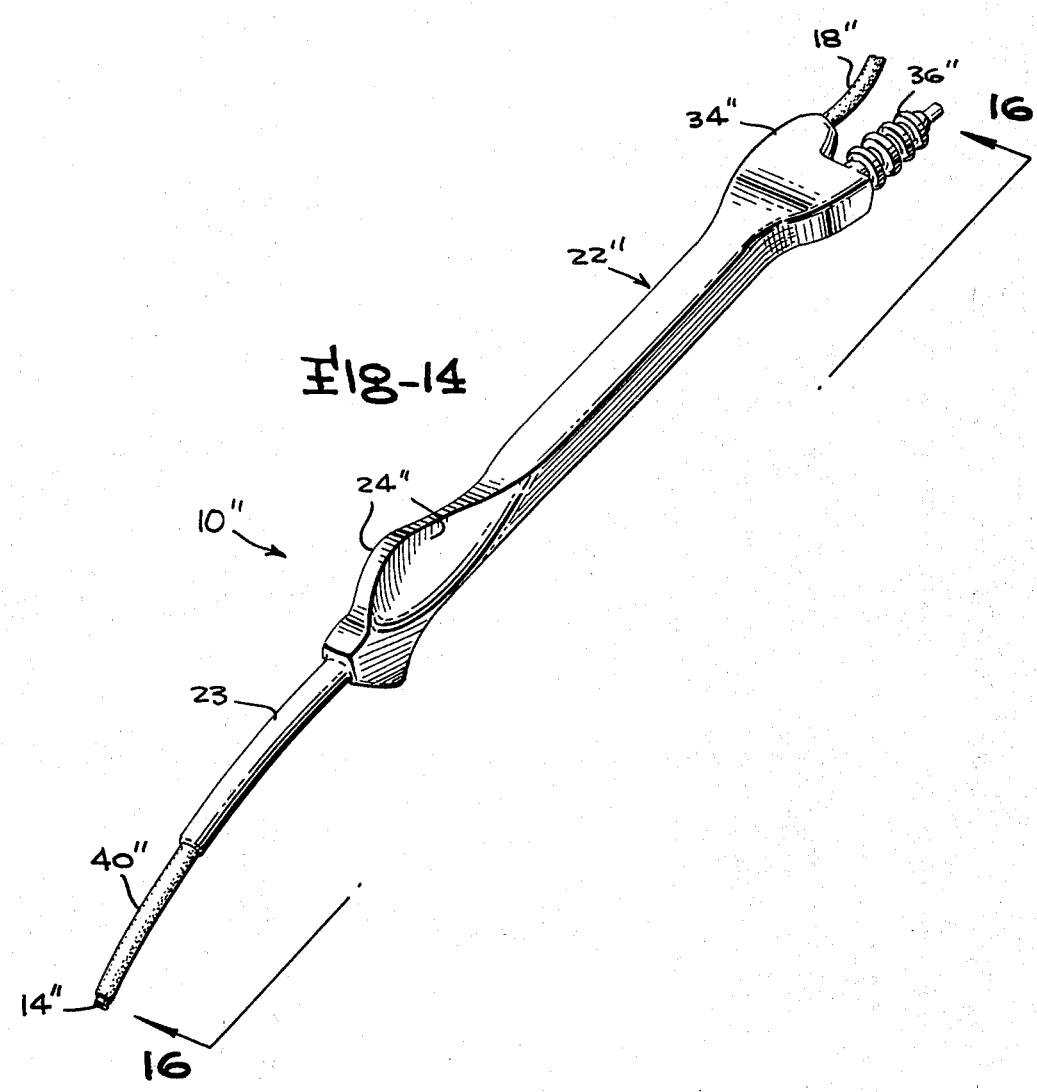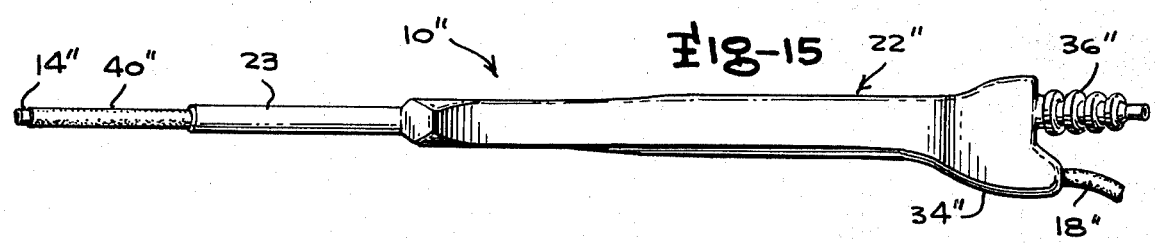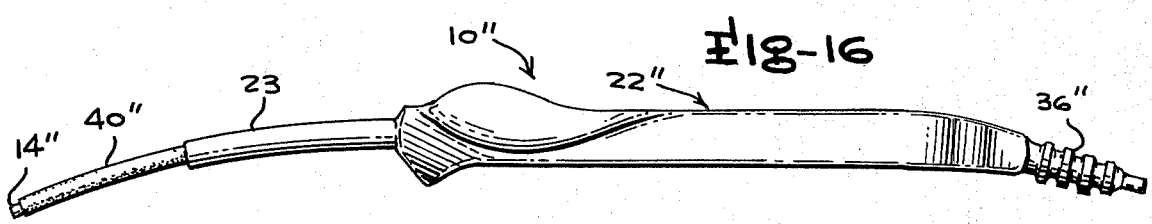

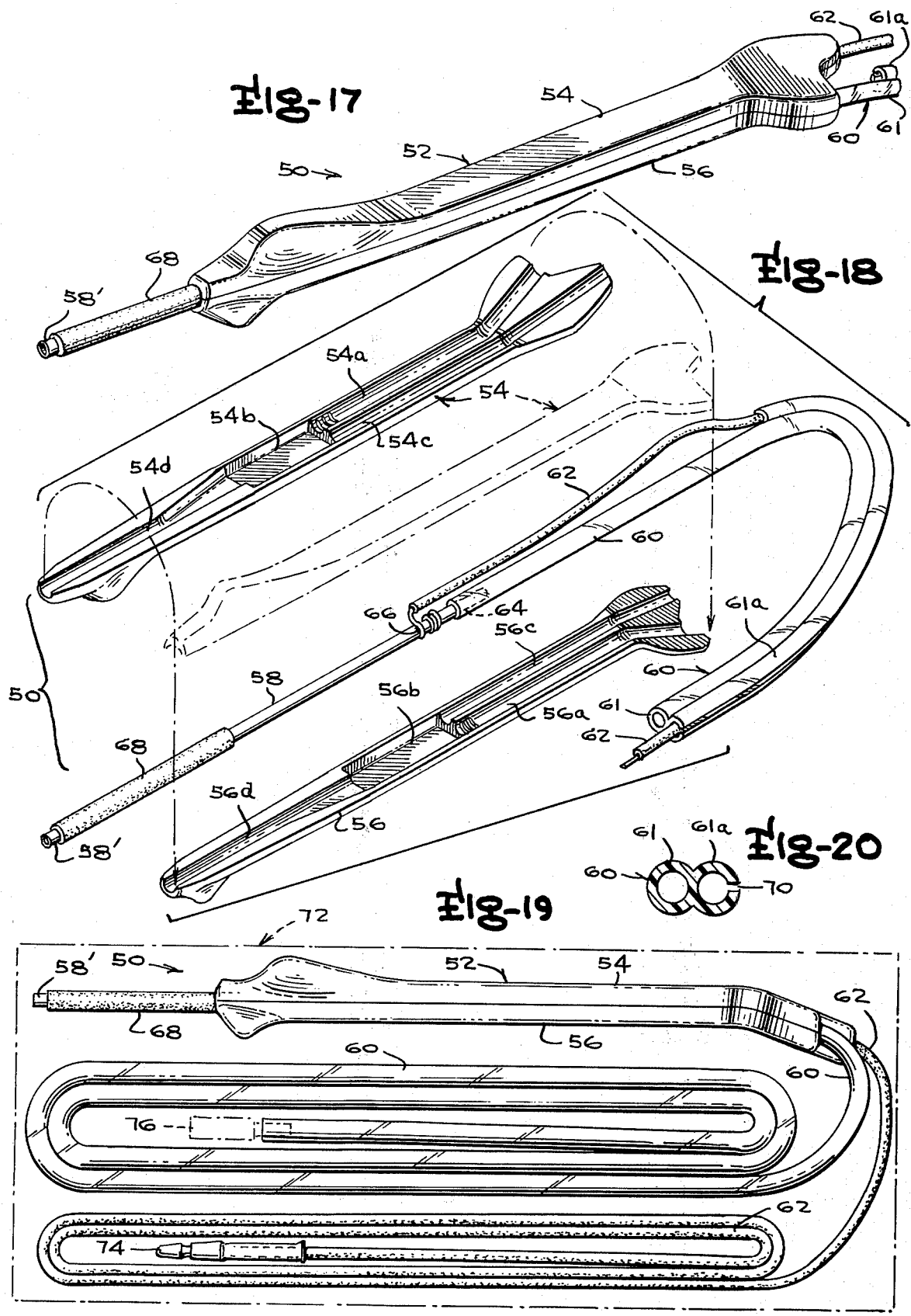

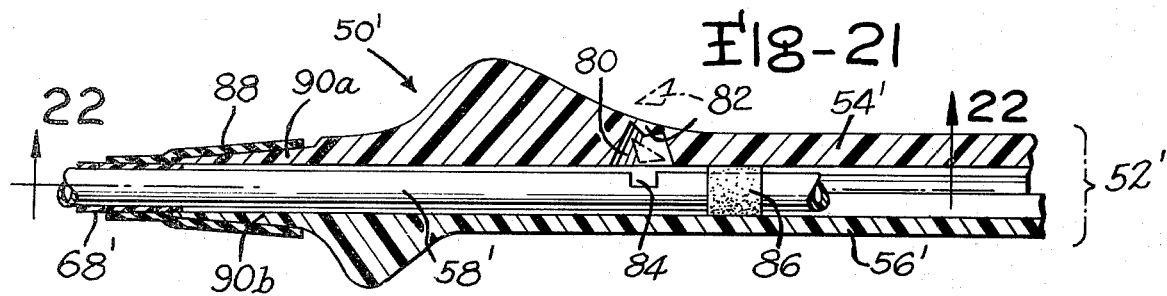
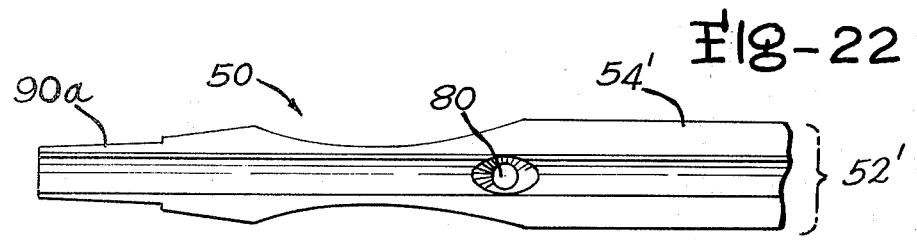
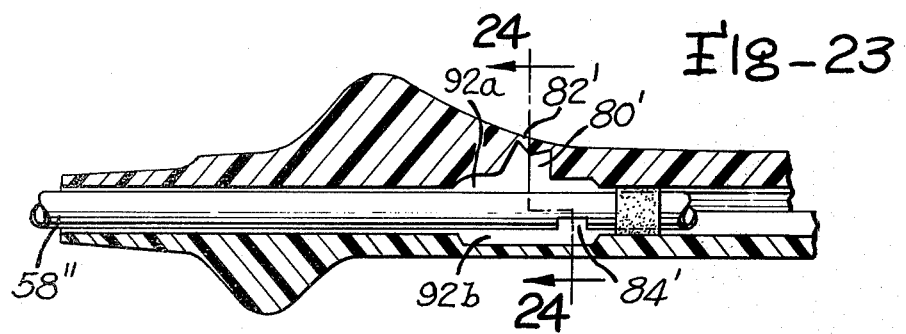
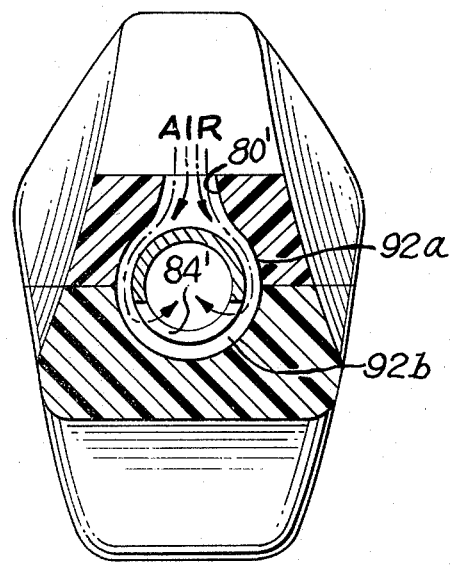

DISPOSABLE ELECTROSURGICAL CAUTERY HAVING OPTIONAL SUCTION CONTROL FEATURE

This application is a continuation-in-part of my co-pending application Ser. No. 342,382, filed Mar. 19, 1973 and scheduled to issue as U.S. Pat. No. 3,825,004, on July 23, 1974.

BACKGROUND OF THE INVENTION

This invention relates to an improved self-contained electrosurgical cautery of the disposable type which preferably is adatped to be prepackaged in sterilized ready-to-use condition.

More specifically the invention relates to disposable electrical cauteries used in a dual capacity to effect the coagulation and/or closing off the terminal portions of severed blood vessels and to simultaneously draw off excess blood from the surgical opening or wound.

The prior art is known to encompass various electrosurgical instruments including some electrical cauteries embodying hand-held electrosurgical electrodes connected through an electrical conductor wire to an electrosurgical unit, some of which utilize an inactive electrode in plate form or the like beneath the patient, and further connect the latter electrode to the electrosurgical unit which is properly grounded.

While some of these prior art devices have provided innovative and improved surgical procedures and results, much of the currently available equipment still suffers from certain of the following disadvantages. 1. Inadequate thermal insulation provided by only thin plastic coatings around relatively thin pencil-like electrodes. These electrodes get unbearably hot, particularly during heavy usage, and must be cooled before the operation can be completed. Such delays endanger the patient and are otherwise costly. 2. Unsafe electrical insulation which evolves from repeated cycles of usage and resterilization, which tend to crack and chip the insulation on known prior art devices. These usually cause short circuits often resulting in electrical burns or shock to the user severe enough to burn holes in rubber operating gloves. Further, this tends to contaminate the operating field, and the surgeon often must continue to operate with painful burns.

3. Unreliable electrical connectors, evolving from the electrical connectors and interconnecting wire being subjected to repeated resterilization whereby they become unreliable after a few uses. Operations are frequently delayed when one of the connectors shorts out and requires repair.

4. Resterilization takes costly time, and they are difficult to sterilize as a result of the time delay between completion of operations and cleansing of the instruments, during which delay blood and other tissue remaining in the sucker tube or barrel of the electrode tends to dry and cling to the inside wall thereof in spite of regular washing. This residue breeds bacteria which is frequently not killed in sterilization because steam and disinfectant gases do not adequately vent through the thin tubing of the barrel. In normal surgical procedure, the barrel often becomes clogged with tissue and must be cleared by inserting a thin wire. Withdrawing this wire brings with it the bacteria lodged there and contaminates the sterile operating field.

5. Poor human engineering has provided present electrodes which are unwieldly and difficult to use with precision. The very thin barrel of the electrode is too small to grip securely, especially with moist surgical gloves; and the heavy rubber tubing and wire connector at the rear of such prior art electrodes make them extremely unbalanced. Furthermore, the separately extended or hanging vacuum tubing and electrical conductor wiring of the prior art cauterizers tend to interfere with and impede efficient surgical and operating room procedures. Also because a cautery's electrical resistance changes after each use, the associated electrical power source must be re-adjusted almost each time.

6. The discomfort and possibility of infection associated with currently available electrodes forces many surgeons to use slower more difficult means of controlling bleeding in spite of the decided advantages offered by cauterization afforded by prior art electrosurgical units such as the CSV BOVIE manufactured by the Ritter Equipment Company, a division of Sybron Corporation.

In order to alleviate the foregoing problems and disadvantages, the present improved inventions were developed and have been successfully used.

SUMMARY OF THE INVENTION

The improved disposable cauterizer of this invention overcomes all of the above problems, and basically consists of an insulated-handle-enclosed metal tube with a conductor wire permanently attached, thus eliminating the bulky connector and avoiding the possibility of a short circuit. A specially contoured plastic handle of generous proportions may be molded over the tube in some embodiments, or otherwise made to permanently cover the junction of the conductor wire. The thick handle provides more than adequate thermal and electrical protection, and its anatomical contour thereby makes the electrode very easy to manipulate.

Prior to use, a flexible hose or sucker tube, connectible with vacuum source, is attached to the proximal portion of the tubular electrode which, in one form, projects from the corresponding proximal end of the handle, and the wire, which is suitably insulated, is connected to a high frequency power source. In another more preferred form, a preferably clear flexible plastic sucker tube is firmly connected to an electrode, and the handle is initially made in two parts having complemental recessed areas and channels therein to receive the assembly of the sucker tube and preattached electrical conductor wire. In this latter form, the hollow stainless steel electrode tube does not project from the rearward or proximal portion of the handle, but terminates approximately midway within the handle, and one end of the preferably clear electrically conductive flexible plastic sucker tube is firmly attached over the end of the handle-enclosed portion of the electrode tube. Both the sucker tubing and electrical conductor wire are of predetermined lengths to reach the respective associated equipment. Provision also is made on the sucker tubing to integrate therewith the electrical conductor wire, at least for preferably several feet in the immediate area of the operating table, to reduce the likelihood of interference by separate tubing and electrical conductor wires otherwise stretched out individually among the patient and operating staff members.

Yet another preferred embodiment contemplates my improved cautery which includes the provision of a selectively establishable suction control hole in the handle and tube, of the type disclosed in the mid-to-latter part of the Abstract of the Disclosure.

In operation, blood from a surgical incision is drawn by a vacuum through the barrel of the electrode and clear of severed vessels, and a high frequency current passing through the electrode cauterizes the ends of the vessels preventing further bleeding. The device of this type is most aptly described as a cauterizer, however, surgeons frequently refer to it as a desiccator or just BOVIE after the power supply with which it is often used. When the control hole is desired, the weakened membrane usually is initially punched out, and which hole can be covered selectively by the finger or thumb to obtain full or partial suction at the tip of the suction tube.

This improved electrode is designed to be disposable after one use and will be shipped from the factory pre-packaged in sterile containers. This guarantees the sterility of the instrument and insures that the connecting wire will not fail due to wear.

Accordingly, it is the principal object of this invention to provide an improved disposable type cautery which will overcome all of the aforementioned disadvantages, and, by embodying the foregoing improved features, may be used in conjunction with existing electrosurgical units.

This and other objects and advantages of the present invention will become apparent from a consideration of the following detailed description taken together with the illustrative drawings.

BRIEF DESCRIPTION OF THE DRAWINGS

FIG. 1 is a perspective view of one embodiment of the improved suction-type cauterizer having a slightly curved electrode probe;

FIG. 2 is a front elevational view taken on line 2—2 of FIG. 1;

FIG. 3 is a rear elevational view of the instrument of FIG. 1;

FIG. 11 is a fragmentary side elevational view of the proximal position of the instrument as viewed on line 11—11 of FIG. 4;

FIG. 14 is a perspective view similar to FIG. 1, but depicting a modified form having a foreshortened handle and reduced size elongated electrode probe adapted more particularly for neurological use;

FIG. 15 is a bottom plan view of the modified form of FIG. 14;

FIG. 16 is a side elevational view of the FIG. 14 form as taken on line 16—16;

FIG. 17 is a perspective view, similar to FIGS. 1 and 14, of a further, preferred embodiment fabricated of two body half members fused together to integrally unite the components therein, and depicting a straight electrode probe therewith;

FIG. 18 is an exploded perspective view of the embodiment of FIG. 17, better showing body recess details and the relative relationship of the component members thereof;

FIG. 19 is a side elevational view of the embodiment of FIGS. 17 and 18 showing folded predetermined lengths of the flexible sucker tubing and electrical conductor wiring associated therewith, and depicted within a broken outlined sterilized package schematically representative of the intended disposable character in which the representative is preferably merchandised;

FIG. 20 is an end view of novel form of flexible sucker tubing preferably having integrally molded or otherwise suitably formed therewith means for integrating the electrical conductor wire in association therewith, as better shown in FIG. 18;

FIG. 21 is a longitudinal fragmentary cross-sectional view representative of a further preferred embodiment, showing provisional for a suction control hole means in the cautery;

FIG. 22 is a view of the upper half of the cautery of FIG. 22, taken substantially on line 22—22 of FIG. 21, and omitting the suction/cautery tubing;

FIG. 23 is a view similar to FIG. 21 showing a still further modification of the form of FIG. 21; and FIG. 24 is an enlarged transverse cross-sectional view taken substantially on line 24—24 of FIG. 23.

DETAILED DESCRIPTION OF EMBODIMENTS

Figure 4:
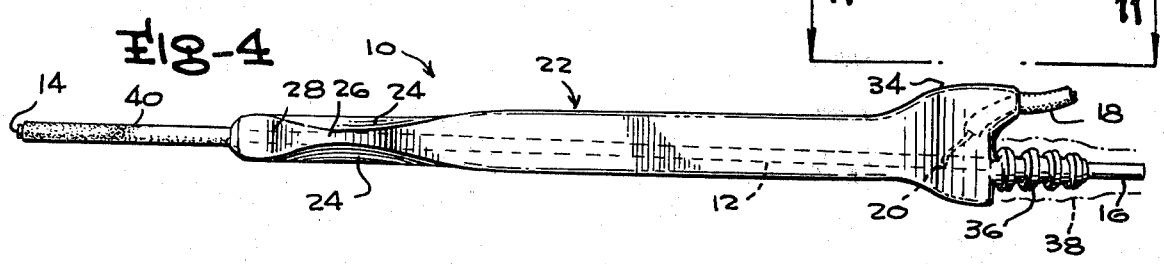
FIG. 4 is a top plan view of the instrument of FIG. 1.

In the preceding and following description, the term distal is understood to refer to the forward-most end most remote from the user, whereas the term proximal refers to the rearward-most end of the cautery closest to the user.

Referring to the form of FIGS. 1–11, the suction cautery is generally designated at 10 and comprises an elongated, electrically conductive metal electrode/-sucker tube 12 terminating in a distal end 14 and a proximal end 16, and having one end of a length of insulated electrical conductor wire 18 permanently attached at 20 (FIG. 4) to a proximal portion of the tube 12. The permanent connection thereof eliminates the necessity of a separate connector fixture, which is often bulky, and avoids the possibility of a short circuit, particularly when the major part of the tube 12 and the end portion of wire 18 are permanently encased in the uniquely anatomically shaped or contour-molded plastic handle 22. The projecting portion of tube 12 of this form is preferably of slightly acruate form in the vertical plane thereof.

Figure 5:
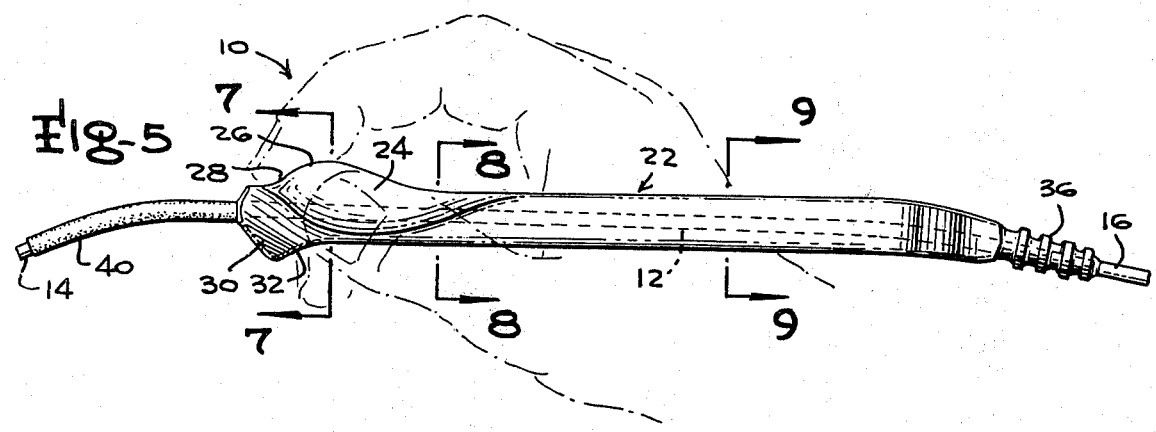
FIG. 5 is a side elevational view of the instrument of FIGS. 1 and 4, the forward half of which is substantially symmetrical about a longitudinal center line.
Figure 6:
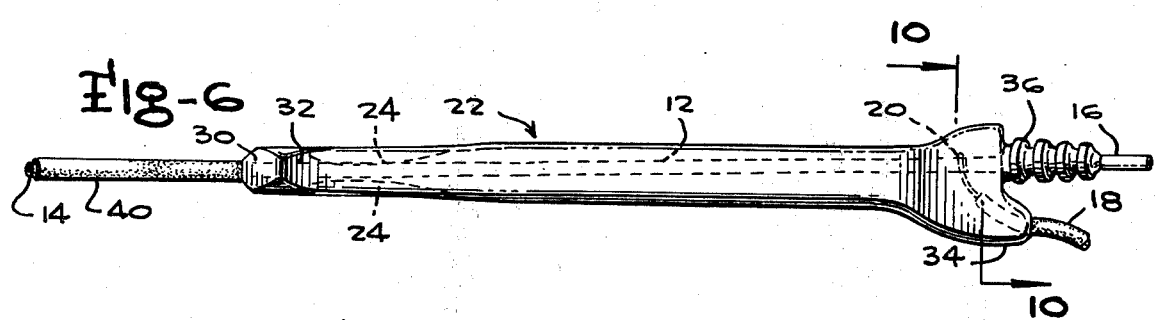
FIG. 6 is a bottom plan view of the instrument shown in FIGS. 1, 4 and 5.
Figure 9:
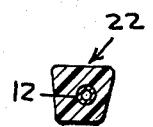
Figure 10:
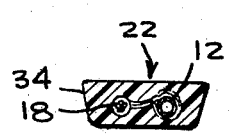
FIG. 10 is a cross-sectional view taken on line 10—10 of FIG. 6.

Handle 22 is of generous proportions and includes opposed distally disposed identical recessed thumb and finger gripping portions 22, 24 and an arcuately raised projection 26 on the top side which smoothly forms a first concave finger rest 28 with the distal extremity of the handle. The handle 22 further includes a generally inverted pyramidal shaped projection 30 on the distally bottom side which blends smoothly with the main body of the handle to form a second concave finger rest 32 therebeneath. The specially contoured handle permits ambidextrous deft and positive gripping of the instrument in the various manners as depicted in FIGS. 1 and 5. While the instrument preferably will be handled primarily in the manners mentioned, the slightly trapezoidal shaped cross-section of the main body, as depicted in FIG. 9, further facilitates a comfortable and positive manipulative grip of the instrument when held at an intermediate portion of the handle.

Preferably, the proximal portion of handle 22 includes a pronounced laterally offset portion 34 which rigidly encases the conductor wire 18. The proximal main body portion further preferably includes an intergrally molded convoluted or annularly ribbed hose-connection nipple 36 to facilitate a good friction fit therewith of a flexible vacuum hose 38 shown in broken outline in FIGS. 1 and 4. The body handle is seen to have substantial thickness, and is fabricated of a plastic or other suitable rigid material having appropriate electrical and thermal insulating qualities. Therefore, it is very comfortable and easy to manipulate.

The distally projecting end of the suction/electrode tube 12 is usually covered with an insulation sleeve 40 beyond the handle 22 to within about ⅛ inch of the end. If desired, the insulation sleeve 40 may extend the full length of the tube and be molded or gripped partially or fully within the handle 22, although this is not necessary in view of the insulative qualities of handle 22. Sleeve 40 may be of tapering or otherwise non-uniform cross-section in an area exposed forwardly of the handle 22 and the coutoured finger gripping area.

The improved disposable cautery electrode is to be factory packaged in sterile containers or envelopes, ready for use upon opening by the doctor. Prior to surgical use, the flexible vacuum hose 38 from a suitable vacuum source is connected to the hose nipple 36, and the conductor wire 18, of predetermined length is connected to a high frequency source of electrical power, such as mentioned in the preamble hereof. During operative use, the accumulating blood from a surgical incision is drawn through the hollow barrel of the tubular electrode 12, clear of the severed blood vessels, and a high frequency electrical current is passed through the electrode to cauterize the vessels and prevent further bleeding.

Figure 12:
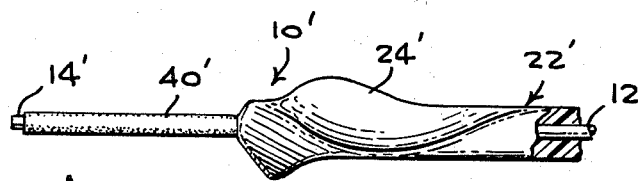
FIG. 12 is a fragmentary side elevational view similar to FIG. 5, but only of the distal probe portion of a modified embodiment having a straight electrode probe, and having a portion of the body broken away.
Figure 13:
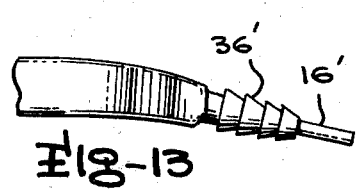
FIG. 13 is a fragmentary side elevational view of the proximal end portion of a modified hose connection portion of the body.
Figure 7:
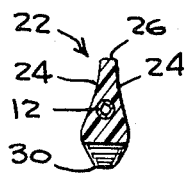
FIGS. 7, 8 and 9 are cross-sectional views as taken substantially on lines 7—7, 8—8, and 9—9 of FIG. 5.
Figure 8:
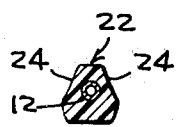

Referring to the modified form of FIGS. 12 and 13, the instrument 10' is essentially identical to the aforedescribed embodiment, except that the distally protruding electrode or point is of straight form, and the proximally extending hose-connecting nipple 36' is of slightly different form from that of the previously described form. Because of the near identical construction of these various forms, the same but primed and double primed reference numbers are being used to designate corresponding parts therein. While separate forms may be provided for different lengths of protruding probes, depending upon preferences of different surgeons, it is contemplated that the tubular electrode is of a sufficiently deformable material whereby the forward probe end can be manually bent or curved to adapt it to different use circumstances.

Further referring to the modified embodiment of FIGS. 14-16, this cautery handpiece, designated generally at 10'', is very much the same as the previous forms except for embodying a foreshortened handle 22'' having an integrally formed, slightly arcuate tubular distal portion 23. The generally cylindrical form of said forward portion 23 lends this embodiment more particularly to neurological use such as in craniotomies, whereby the reduced diameter of the probe end will readily pass through holes surgically drilled in the patient's skull.

Referring next to the further preferred embodiments depicted in FIG. 17-20, they are representative of improved features now to be described in more detail.

The cautery assembly of this embodiment is quite similar in most respects to the first described embodiments, and is generally denoted by the numeral 50 having an initially two-part handle 52. Said handle 52 includes an upper half member 54 and a lower half member 56. Said members are suitably internally recessed and channeled to receive, and are subsequently fused together around the preferably stainless steel electrode tube 58 and adjoining flexible plastic sucker tubing 60 and electrical conductor wiring 62. It is noted that the electrode tube 58 is very similar in construction and identical in function to the counterpart tubes 12 and 12' of the other embodiments. The main difference is that tube 58 has a proximal terminal end portion 64 which terminates within a generally medial portion of the composite handle 52. The presterilized sucker tubing 60 is preferably simply slip fitted over the end 64 of tube 58, as shown, and the adjacent portion of the flexible plastic tubing is received within preferably snug-fitting complementary recessed channels 54a and 56a in the body members.

Distally of the connection of the flexible tubing 60 upon the electrode tube end 64, is the preferably permanent connection of the insulated electrical conductor wire 62 to the metal electrode tube 58. The conductor wire is stripped of its insulation for a short area and wrapped and suitably soldered or brazed to said tube 58, as shown at 66 in FIG. 18. Recessed provision, preferably in the form of opposed complemental recesses 54b and 56b, is made to readily accommodate the aforedescribed connections. Furthermore, the proximal portions of the handle members 54 and 56 also include preferably complemental recessed channels 54c and 56c respectively, to receive and firmly grip therein the lead end portion of the electrical conductor wire 62.

Additionally, the distal portions of said handle members are provided with preferably complemental recesses 54d and 56d to receive therebetween both a major portion of the electrode tube 58, and also preferably a portion of the overlying insulating sleeve 68 provided around the distally exposed portion of the electrode tube or probe 58. The distal most tip end 58' is left bare, as mentioned in the first-described embodiments.

The general overall configuration and handle contours, particularly in the distal finger-gripping areas, remain essentially like those of the first-described embodiments, after the handle members are fused together.

It is contemplated that the handle members may be initially fabricated in vertically divided half members rather than in the illustrated horizontally divided manner, in which case any offset tail portion would be generally vertically disposed, if used, rather than horizontally as shown.

While the handle members may be joined together in any suitable manner, either mechanically or adhesively, a preferred form is by the fusing together by the application or ultrasonic vibrations to the assembled handle components.

Straight or curved probe ends of the electrode tube may be provided as desired, as well as a similar distally projecting reduced cross section of the body handle corresponding to that of member 23 in the embodiment of FIG. 14.

In each of the foregoing embodiments, the flexible plastic tubing 60 is to be of an electrically conductive nature so that when in use it will ground and dissipate any tendency to build up static electricity which is known to be capable of exploding ether or other ambient gases having a propensity to ignite or explode.

FIGS. 18 and 20 more particularly illustrate the novel form of the flexible tubing 60 which I prefer to use in conjunction with all embodiments. Tubing 60 comprises the usual basic full tubing conduit 61, and a second integrally formed longitudinally split conduit portion 61a within which conduit portion the insulated electrical conductor wire 62 is adapted to be substantially fully and removably disposed. In the illustrated FIG. 18 embodiment, due to the use of separate channel-like recesses for the tubing 60 and wiring 62, the second split conduit portion 61a is either removed from or not originally fabricated with the basic tubing conduit 61 for the extent of which is housed within the handle 52. Preferably the second, split conduit portion commences closely behind the proximalmost end of the handle, and may be co-extensive with the full length or any lesser predetermined portion of the flexible tubing 60, dependent upon the particular circumstances relating to the type and relative disposition of the vacuum and power source equipment with which they are attachable. Primarily the flexible tubing and electrical conductor wire are co-extensively joined for a sufficient common length so as to greatly reduce the degree of potential interference by otherwise using two lines separately in the immediate area of the operating table and attending staff members. While the second split conduit 61a is shown as a complete conduit which is longitudinally split, it also may be in the form of a discontinuous conduit, or spaced split conductor-wire-fastener rings or bands. Furthermore, in some other preferred forms, the split, designated 70, which may be oriented in different peripheral portions, is made to have a positive longitudinal spacing to better facilitate insertion and removal of the cable 62.

In merchandising the pre-sterilized cautery assembly of this invention in individual envelope or container form, designated schematically at 72 in FIG. 19, it is to be understood that the conductor wire 62 preferably would be integrated within the split conduit 61a, although not shown as such in said FIG. 19. The conductor wire 62 is preferably provided with an electrical jack 74 of a suitable form to fit complementally into a power source with which it is adapted to be used. While a preferred size of the flexible vacuum tubing 60 may be of ⅛ inch I.D., it also may be made of other various sizes or, may be provided with a suitable adaptor means 76 (FIG. 19) to facilitate joining with other size tubing or tubing connections on the associated equipment.

The handles 22 and 52 are preferably made of an opaque plastic material and may be provided in various colors, if desired, although an opaque white has been found very acceptable and maintains a very antiseptic appearance of the presterilized instruments. Due to the nature of the surgical use to which these instruments are subjected, and the problems encountered among various of the unsatisfactory prior art devices, it was necessary to evolve any expendable electrode cautery to completely avoid any possible contamination which otherwise might arise from a previous use. Accordingly, the improved cauteries of this application were simply and economically designed to be exceptionally dependable as well as disposable while embodying the improved functional features lending themselves to be economically, functionally, dependably and aesthetically attractive.

Reference next will be made to the suction control hole embodiments depicted representatively in FIGS. 21–24, forming the main basis of this continuation-in-part application.

Some surgeons prefer to use an electrosurgical cautery having the suction control hole feature to enable them to have control over the suction or vacuum in a suction-integrated cautery of this type. Control of the vacuum or suction feature permits the surgeon to interrupt the formed vacuum and thereby preclude potential increase of wound trauma when applying the electrode to the tissue and severed vessels for coagulation. This control thereby precludes the electrode from tending to "kiss" onto or otherwise become unduly attached to the tissue in contact therewith, which attachment may cause the tissue to stretch and tear during removal of the electrode.

Suction control means for other electrosurgical cauteries has been known heretofore. The simplest means of obtaining suction control in the improved cauteries of this and my preceding applications, appears to be by placement of a vent hole in the barrel of the cautery/suction tube, and adjacent insulative handle.

In FIGS. 21 and 22, the cautery per se is designated generally as 50', with similar parts designated by the same but primed reference numerals as those used relative to FIGS. 17–20, where applicable. The upper portion 54' of the handle 52' is preferably provided with an integrally formed or molded holelike potential suction-control cavity 80 covered by a thin, peripherally weakened membrane 82 which can be readily punched out when desired, as by a small hemostat, probe, or other small relatively blunt instrument. Correspondingly aligned adjacent to the cavity 80, the cautery/suction tube 58' is provided with an aperture 84 for cooperation with cavity 80 when it is punched out.

The covering membrane is preferably of inverted cone shape, as shown, and the hole 80 is preferably of increasing area size inwardly of the membrane cover 82. This enables the free passage of air past the membrane cover in instances where it is forced and dislodged in whole or part inwardly as shown in dotted lines in FIG. 21. The membrane cover 82 may also be punched loose and pried or tweezered exteriorly of the cavity 80.

A soft plastic seal 86, preferably of tubular form encircles the tube 58' rearwardly of the cavity 80 and tube hole 84, to preclude unwanted air leakage into the suction control hole from the rearwardly disposed cavities in instances where the body halves do not completely fuse together or otherwise seal peripherally around the projecting suction tubing and electrode wiring, as described more particularly in the previous embodiment of FIGS. 17–20.

No separate seal similar to seal 86 is required forwardly because the sealed juncture of the two body halves particularly forward of the tube hole 84 is assured by either the sandwiching therebetween of the end of insulating sleeve 68' (FIG. 21) like that in FIGS. 17–20, and/or due to an auxiliary optional outer combined insulating and body-halve securing sleeve 88. Preferably sleeve 88 is of a character and size to give an exceptionally close fit around complementary preferably tapered, distal end portion 90a and 90b of the upper and lower handle halves 54' and 56' respectively. The auxiliary sleeve may be of a heat-shrinkable character to provide such an inherent sealing fit, and usually terminates closely adjacent the distalmost ends of portions 90a and 90b.

Suction control is considered to be a matter of personal preference, some surgeons considering it to be a nuisance to have to cover the hole each time full suction is desired, while others insist on having this feature. Thus, the improved cauteries of this application provide the surgeon with the selective choice of having it or not having it.

Reference to FIGS. 23 and 24 discloses a further modification of the basic embodiment of FIGS. 21 and 22. In this latter form the usually closely fitting recesses, in the handle portions for the cautery/suction tube 58" are of enlarged size in the area 92a and 92b of the control apeature 84' therein. The same type knockout membrane cover 82' preferably is used in the form also.

Provision of the enlargement both radially and axially around tube suction hole 84' will facilitate manufacture and assembly by eliminating the need to carefully align the tube or barrel aperture with the cavity or hole 80' in the plastic handle portion.

It is apparent that the enlarged area will permit the flow of sufficient air regardless of the orientation of the tube hole 84' relative thereto.

Accordingly, when the cavity is initially unpunctured and left covered, no suction control is available. When the cavity is opened or unobstructed, no suction is created at the distal end of the probe unless selectively covered by a thumb or finger of the surgeon using the cautery instrument. Upon release of the covering digit, entry of atmospheric air is permitted to the suction line or tubing and probe, thereby decreasing or eliminating the vacuum at the probe tip.

While thus far the foregoing descriptions have been concerned primarily with the mechanical structure and details, it is understood that certain novel process procedures may be present attendant the fabrication of these various cauterizer embodiments.

From the foregoing detailed and illustrative drawings descriptions, it is apparent that improved cautery means have been provided which achieve the objectives and advantages set forth in the preamble hereof. Various changes and alterations may be made to the various forms, which changes may include the formation of the contoured finger gripping areas by use of other than the visibly raised and/or depending projections on the handle, assuming at least the upper contour could be recessed and generally concealed in side view by laterally and vertically extended handles or the like. Also, the laterally offset proximal handle portion could be divided equally to each side of the handle or the handle be made of slightly diverging form in the proximal part to encase the wire and tube without noticeable offset areas. And the curvatures of said distal tube portions may be in various planes if desired to suit specific surgical needs. Because those skilled in the art may make changes in details without departing from the spirit of the invention, reference should be had to the appended claims for the scope of coverage afforded thereby

I claim:

1. In a hand-operated electrosurgical cautery instrument constructed particularly for single occasion use as a disposable combination cauterizer electrode and sucker tube, adapted for use with remotely located vacuum source means and electrical high frequency current source and control means, the improvement wherein said cautery instrument comprises:
   a. sucker tube means including an elongated metallic tube of small diameter adaptable for entry into surgical cavities, said tube constituting an electrode and at least a partial sucker tube combination having distal, intermediate and proximal portions; said proximal portion adapted to be connected with a flexible tubing for connection with said vacuum source means;
   b. handle means embracing and in sealed relationship with at least an intermediate portion of said sucker tube;
   c. a flexible electrical conductor wire of predetermined length having one end electrically connected to a portion of said electrode tube which is embraced by said handle means; said wire extending from and being insulated exteriorly of said handle means, and having the other wire end free and adapted to be electrically connected with said source of high frequency power;
   d. said handle means including a specially contoured handle having substantial cross-sectional thickness and good thermal and electrical insulating characteristics, and unitarily surrounding a substantial portion of said electrode tube length, including complete fail-proof enclosure of said conductor wire connection with said electrode tube, said handle terminating short of and freely exposing a substantial distal portion of said electrode tube, and having a generally elongated intermediate portion, and said handle further having a proximal end portion, and having a generally distal end portion embodying plural compound curvatures defining plural digital grippping portions to provide for positive deft manipulation of said instrument in use; and
   e. said handle means and sucker tube collectively having selectively establishable suction control cavity means including:
      1. an internal, recessed suction control cavity in said handle means surrounding said intermediate portion of said sucker tube;
      2. an aperture in said sucker tube generally adjacent said recessed suction control cavity; and
      3. an externally accessible frangible membrane in said handle means initially integrally covering said suction control cavity and adapted to be selectively manually breachable as preference may dictate.

2. An instrument as defined in claim 1, wherein said distal portion of said electrode tube which is not enclosed by said handle is enveloped by a sleeve of an electrically insulative material.

3. An instrument as defined in claim 1, wherein said distal portion of said electrode tube which is not enclosed by said handle is enveloped by a sleeve of an electrically insulative material having a generally uniform and substantially less cross-sectional thickness than that of said handle.

4. An instrument as defined in claim 1 wherein said handle means includes composite complementally abuttable handle members having distal portions of reduced cross-sectional size from the rest of said handle members and collectively tapering to a free end portion distally of said instrument, and further including sucker-tube-sleeve insulating means surrounding both essentially all of the distal end of the sucker/electrode tube which projects distally from said handle, and said reduced cross-sectional size distal tapering portions of said handle.

5. An instrument as defined in claim 1, wherein said contoured handle is provided with a laterally widened portion to fixedly and unitarily encase therein said interconnected wire and proximal portion of said electrode tube, in a fail-safe permanent manner.

6. An instrument as defined in claim 1, wherein said handle-formed, plural digital gripping portions include at least a pair of oppositely disposed finger-and-thumb gripping portions symmetrically formed in laterally opposed sides of said handle toward a distal portion, to provide for ambidextrous use of said instrument.

7. An instrument as defined in claim 6, further including a second pair of digital receiving contoured areas formed in opposed top and bottom surfaces of said handle adjacent said first-mentioned gripping portions, said second pair of recesses being longitudinally offset from one another in the distal portion of said handle, to particularly receive forefinger and index finger gripping thereof along with simultaneous thumb gripping in one of said laterally opposed recesses.

8. An instrument as defined in claim 1, wherein said electrical conductor wire of paragraph (b) is permanently electrically connected to a generally proximal portion of said electrode tube.

9. An instrument as defined in claim 1, wherein said distal portion of said electrode tube which is not enclosed by said handle is of manually bendable form and adapted to be of slightly curved form.

10. An instrument as defined in claim 9 wherein said curved tube portion is in a vertical plane so as to tend to point downwardly when held in one operative use position.

11. An instrument as defined in claim 10, wherein said electrode tube is also curved slightly downwardly along a proximal portion and generally co-planar with the distal end curvature, said proximal curvature being such as to be embodied and generally concealed within said handle.

12. An instrument as defined in claim 1 wherein said handle at its distal portion further includes a substantially reduced and generally circular cross-sectional handle portion integrally formed therewith and projecting longitudinally distally therefrom, said reduced cross-sectional portion being of a size to facilitate insertion into surgically drilled holes in a patient's skull during the performance of craniotomies.

13. An instrument as defined in claim 12 wherein said reduced cross-sectional distal handle portion and said distal portion of said electrode tube are both of gently arcuate form.

14. An instrument as defined in claim 12, wherein said distal portion of said electrode tube which is not enclosed by said handle is enveloped by a sleeve of electrically insulative material having a generally uniform cross-sectional thickness which is substantially less than that of said handle portions.

15. An instrument as defined in claim 1 wherein said handle comprises two basic longitudinally split half portions which are integrally joined together in a permanent manner about portions of the sucker tube and conductor wire components of paragraphs (a) and (c).

16. An instrument as defined in claim 15, wherein said handle portions are divided generally horizontally into complementally adjoining upper and lower half members.

17. An instrument as defined in claim 16 wherein said handle portions are provided with complementally opposed recessed areas throughout at least a substantial length of each handle portion, said recessed areas adapted to receive at least portions of both said combined electrode and sucker tube means and also attached portion of said electrical conductor wire.

18. An instrument as defined in claim 1, wherein said metal electrode tube has its proximal portion terminating within said handle, and said sucker tube means further includes a predetermined length of said flexible tubing as an integral part thereof, one end of which is affixed in operative connection with said proximal portion of said electrode tube, and said flexible tubing having a portion integrally enclosed within said handle, and said tubing further including a length extending from a generally proximal portion of said handle.

19. An instrument as defined in claim 18, wherein said flexible sucker tubing is basically of non-metallic material but includes integrally formed means enabling it to have electrically conductive characteristics which when grounded precludes build-up of electrostatic charges.

20. An instrument as defined in claim 18, wherein said flexible sucker tubing includes a basic fluid conduit, and a second longitudinally split conduit integrally formed coestensively therewith for at least a partial predetermined extent thereof exteriorly of said handle; said split conduit adapted to removably receive therein in an integrated manner the said electrical conductor wire for at least part of said predetermined length adjacent to said handle.

21. An instrument as defined in claim 18, wherein said flexible sucker tubing includes a basic fluid conduit, and integrally conductor-wire-fastener means formed with said sucker tubing.

22. An instrument as defined in claim 1, wherein said composite handle includes a pair of longitudinally divided complementary handle members each having complementally mating opposed recessed channels throughout a substantial length thereof to receive said sucker tube means and an adjoining portion of said electrical conductor wire.

23. An instrument as defined in claim 1, wherein said suction control cavity is formed nearly completely through a wall of said handle and is in general alignment with said suction control hole provided in said electrode/sucker tube; said handle wall exteriorly adjacent said suction control cavity constituting said integral frangible membrane covering for said cavity, and said membrane being of pheripherally weakened form to facilitate a manual breachable selective removal when preferred to have a suction control feature with said cautery instrument.

24. An instrument as defined in claim 23, wherein said suction cavity is of size progressively increasing in cross-sectional area inwardly away from said weakened membrane cover.

25. An instrument as defined in claim 1, wherein said suction control hole means in said sucker tube include anhole through a side wall portion thereof; and further including sealing means adjacent said suction hole in said sucker tube to preclude potentially undesired air flow from other portions of said instrument.

26. An instrument as defined in claim 25, wherein said handle is provided with an internal enlargement radially and axially adjacent to and communicating with said suction control cavity means, and said suction control hole in said sucker tube, thereby facilitating assembly of the instrument sucker tube and handle components without particular need to carefully align said suction control hole and said suction control cavity.

27. In a hand-operated electrosurgical cautery instrument embodying a combination cauterizer electrode and sucker tube, the instrument being adapted for use with remotely located vacuum source means and electrical high frequency current source and control means, handle means having electrical and thermal insulating characteristics fully embracing and in sealed relationship with at least an intermediate portion of said combination electrode and sucker tube and terminating short of and freely exposing a substantial distal portion of said electrode/sucker tube, a flexible electrical conductor wire of predetermined length having one end electrically connected to a portion of said electrode tube which is embraced by the handle means, the wire extending from a generally proximal portion and being insulated exteriorly of said handle means for connection with said electrical power source; the improvement comprising in combination therewith:
 a. a suction control hole provided in said electrode/sucker tube in an area within the sealed portion of said handle means;
 b. suction control cavity means formed internally in said handle means generally adjacent said suction control hole in said electrode/sucker tube; and
 c. said handle means including a frangible layer overlying its said suction control cavity means and constituting a unitarily formed membrane cover thereof which is adapted to be selectively removed to establish a suction control feature with said instrument or may be left undisturbed and in place as desired by the user.

28. An instrument as defined in claim 27 wherein said handle is provided with an internal enlargement radially and axially adjacent to and communicating with said suction control cavity means, and said suction control hole in said sucker tube, thereby facilitating assembly of the instrument sucker tube and handle components without particular need to carefully align said suction control hole and said suction control cavity.

29. An instrument as defined in claim 27, wherein said distal portion of said electrode tube which is not enclosed by said handle is enveloped by a sleeve of an electrically insulative material having a generally uniform and substantially less cross-sectional thickness than that of said handle.

30. An instrument as defined in claim 27, wherein said handle means includes composite complementally abuttable handle members having distal portions of reduced cross-sectional size from the rest of said handle members and collectively tapering to a free end portion distally of said instrument, and further including sucker-tube-sleeve insulating means surrounding both essentially all of the distal end of the sucker/electrode tube which projects distally from said handle, and said reduced cross-sectional size distal tapering portions of said handle.

31. An instrument as defined in claim 27, wherein said electrical conductor wire is permanently electrically connected to the generally proximal portion of said electrode tube.

32. An instrument as defined in claim 27, wherein said distal portion of said electrode tube not enclosed by said handle is of manually bendable form and adaptable to be of slightly curved form.

33. An instrument as defined in claim 27, wherein said handle comprises two basic longitudinally split half portions which are integrally joined together in a permanent manner about portions of the sucker tube and conductor wire components.

34. An instrument as defined in claim 27, wherein said suction cavity means includes a cavity of a size progressively increasing in cross-sectional area inwardly away from said frangible membrane cover.

35. An instrument as defined in claim 27, further including sealing means adjacent said suction control hole in said sucker tube to preclude potentially undesired air flow from other portions of said instrument.

36. An instrument as defined in claim 27, wherein said handle at its distal portion further includes a substantially reduced and generally circular cross-sectional handle portion integrally formed therewith and projecting longitudinally distally therefrom, said reduced cross-section portion being of a size to facilitate insertion into surgically drilled holes in a patient's skull during the performance of craniotomies.

37. An instrument as defined in claim 27, wherein said metal electrode tube has its proximal portion terminating within said handle, and said sucker tube means further includes a predetermined length of said flexible tubing as in an integral part thereof, one end of which is affixed in operative connection with said proximal portion of said electrode tube, and said flexible tubing having a portion integrally enclosed within said handle, and said tubing further including a length extending from a generally proximal portion of said handle.

38. An instrument as defined in claim 27, wherein said flexible sucker tubing is basically of non-metallic material but is comprised of a composition enabling it to have electrically conductive characteristics which when grounded precludes build-up of electrostatic charges.

* * * * *